US006869925B1

(12) United States Patent
Eisenberg et al.

(10) Patent No.: US 6,869,925 B1
(45) Date of Patent: *Mar. 22, 2005

(54) INHIBITION OF RETROVIRUS INFECTION

(75) Inventors: Stephen Eisenberg, Boulder, CO (US); Sharon M. Wahl, North Potomac, MD (US); Robert C. Thompson, Boulder, CO (US)

(73) Assignees: Amgen Inc., Thousand Oaks, CA (US); The United States of America as represented by the Department of Health and Human Services, Washington, DC (US)

( * ) Notice: Subject to any disclaimer, the term of this patent is extended or adjusted under 35 U.S.C. 154(b) by 898 days.

This patent is subject to a terminal disclaimer.

(21) Appl. No.: 08/485,438

(22) Filed: Jun. 7, 1995

Related U.S. Application Data

(63) Continuation-in-part of application No. 08/209,040, filed on Mar. 9, 1994, now abandoned, which is a continuation-in-part of application No. PCT/US93/08486, filed on Sep. 9, 1993, which is a continuation-in-part of application No. 07/943,369, filed on Sep. 9, 1992, now abandoned.

(51) Int. Cl.$^7$ ........................ A61K 38/57; C12N 15/15; C07K 14/81

(52) U.S. Cl. ........................... 514/2; 435/69.2; 530/350

(58) Field of Search ............................. 514/2; 435/69.2, 435/172.3, 252.3, 69.1; 530/350, 324; 424/2; 536/23.5

(56) References Cited

U.S. PATENT DOCUMENTS

| | | | | | |
|---|---|---|---|---|---|
| 4,394,443 | A | * | 7/1983 | Weissman et al. | 435/6 |
| 4,511,503 | A | * | 4/1985 | Olson et al. | 530/422 |
| 4,530,901 | A | * | 7/1985 | Weissman | 435/69.51 |
| 4,546,082 | A | * | 10/1985 | Kurjan et al. | 435/172.3 |
| 4,595,674 | A | * | 6/1986 | Tschesche et al. | 514/9 |
| 4,626,510 | A | * | 12/1986 | Grandi | 435/320.1 |
| 4,652,639 | A | * | 3/1987 | Stabinsky | 435/91.52 |
| 4,672,032 | A | * | 6/1987 | Slavkin et al. | 435/68.1 |
| 4,711,848 | A | * | 12/1987 | Insley et al. | 435/69.2 |
| 4,720,454 | A | * | 1/1988 | White et al. | 435/6 |
| 4,760,130 | A | * | 7/1988 | Thompson et al. | 530/350 |
| 4,788,135 | A | * | 11/1988 | Davis et al. | 435/6 |
| 4,829,052 | A | | 5/1989 | Glover et al. | 514/12 |
| 4,845,076 | A | * | 7/1989 | Heinzel et al. | 514/2 |
| 4,891,356 | A | | 1/1990 | Szabo | 514/2 |
| 4,916,117 | A | | 4/1990 | Lezdey et al. | 514/8 |
| 4,923,807 | A | * | 5/1990 | Webb et al. | 435/69.2 |
| 4,952,512 | A | | 8/1990 | Loskutoff et al. | 435/320.1 |
| 5,102,995 | A | * | 4/1992 | Tollefesen et al. | 536/23.5 |
| 5,109,113 | A | * | 4/1992 | Caras et al. | 530/350 |
| 5,134,119 | A | | 7/1992 | Lezdey et al. | 514/8 |
| 5,151,438 | A | * | 9/1992 | Sham et al. | 514/357 |
| 5,151,509 | A | | 9/1992 | Kotwal et al. | 536/23.7 |
| 5,157,019 | A | * | 10/1992 | Glover et al. | 514/12 |
| 5,196,404 | A | * | 3/1993 | Maraganore et al. | 513/13 |
| 5,215,915 | A | | 6/1993 | Tiberi et al. | 435/252.3 |
| 5,252,725 | A | * | 10/1993 | Rubin et al. | 536/23.5 |
| 5,290,762 | A | | 3/1994 | Lezdey et al. | 514/8 |
| 5,376,633 | A | | 12/1994 | Lezdey et al. | 514/8 |
| 5,514,662 | A | | 5/1996 | Seman et al. | 514/31 |
| 5,532,215 | A | | 7/1996 | Lezdey et al. | 514/8 |
| 6,017,880 | A | * | 1/2000 | Eisenberg et al. | 514/12 |
| 6,132,990 | A | * | 10/2000 | Bandyopadhyay et al. | 435/69.2 |

FOREIGN PATENT DOCUMENTS

| | | | |
|---|---|---|---|
| EP | 0114506 | * | 8/1984 |
| EP | 0 346 500 B1 | | 7/1994 |
| WO | WO 84/03711 | * | 9/1984 |
| WO | WO 86/03497 | * | 6/1986 |
| WO | WO 86/03519 | * | 6/1986 |
| WO | WO 93/09791 | | 5/1993 |

OTHER PUBLICATIONS

Kueppers, F., Biochimica et Biophysica Acta, vol. 299, "Proteinase inhibitor in human tears", pp. 845–849, 1971.*

Wallner, O., et al., Hoppe–Seyler's Z. Physiol. Chem., vol. 355, "Characterization of an acid–stable proteinase inhibitor in human cervical mucus", pp. 709–715, 1974.*

Burnon, D. E., et al., "Activity of some peptide hydrolase enzymes in fresh and stored poultry semen from full sib groups of males and their relation to fertility", Chemical Abstracts, vol. 84, No. 28236, 1975.*

Schiessler, H., et al., Hoppe–Seyler's Z. Physiol. Chem., vol. 357, "Inhibitors of acrosin and granulocyte proteinases from human genital tract secretions", pp. 1251–1260, 1976.*

Ohlsson, K., et al., Hoppe–Seyler's Z. Physiol. Chem., vol. 358, "Isolation and partial characterization of a low molecular weight acid stable protease inhibitor from human bronchial secretion", pp. 583–589, 1977.*

Scheissler, H., et al., in Neutral Proteases of Human Polymorphonuclear Leukocytes, Havemann, K., et al., Eds., "Acid stable inhibitors of granulocyte neutral proteases in human mucous secretions . . . ", Chemical Abstracts, vol. 89, No. 192866u, 1978.*

Fritz, H., et al., Agents and Actions, vol. 8, "Naturally–occurring low molecular weight inhibitors of neutral proteinases from PMN–granulocytes and of kallikreins", pp. 57–64, 1978.*

Scheissler, H., et al., in Human Fertilization, Ludwig, H., et al., Eds., "Inhibitors of granulocyte proteases (antileukoprotease) in human genital tract secretions," pp. 101–106, 1978.*

Lovett, P. S., et al., Methods in Enzymology, vol. 68, "*Bacillus subtilis* as a host for molecular cloning", pp. 342–357, 1979.*

(List continued on next page.)

*Primary Examiner*—Ponnathapura Achutamurthy
*Assistant Examiner*—William W. Moore
(74) *Attorney, Agent, or Firm*—Finnegan, Henderson, Farabow, Garrett & Dunner, L.L.P.

(57) ABSTRACT

Methods and pharmaceutical compositions are provided to prevent retroviral infections of host cells. More particularly, the invention relates to prevention of HIV infection of human cells by serine leukocyte protease inhibitor (SLPI).

22 Claims, 2 Drawing Sheets

OTHER PUBLICATIONS

Schleisser, H., et al., “Inhibitors of granulocyte protease (antileukoprotease) in human genital tract secretions”, Chemical Abstracts, vol. 90, No. 117084e, 1979.*

Movva, N. R., et al., Journal of Molecular Biology, vol. 143, “Gene structure of the OmpA protein, a major cell surface protein of *Escherichia coli* required for cell–cell interaction”, pp. 317–328, 1980.*

Fritz, H., in Protein Degradation in Health and Disease, Ciba Foundation Symposium, “Proteinase inhibitors in severe inflammatory processes (septic shock and experimental endotoxaemia): biochemical, pathophysiological and therapeutic aspects”, pp. 351–, 1980.*

Svendsen, I., et al., “Amino acid sequence homology between a serine protease inhibitor from barley and potato inhibitor I”, Chemical Abstracts, vol. 95, No. 2484w, 1981.*

Chandrasekar, M., et al., “Synthesis of a fragment of the active center of serine proteases”, Chemical Abstracts, vol. 95, No. 169751, 1981.*

Miller, W. L., et al., Drug Development Research, vol. 1, “Synthesis of biologically active proteins by recombinant DNA technology”, pp. 435–454, 1981.*

Hewick, R. M., et al., Journal of Biological Chemistry, vol. 256, “A gas–liquid solid phase peptide and protein sequenator”, pp. 7990–7997, 1981.*

Kurachi, K., et al., Proceedings of the National Academy of Sciences, U.S.A., vol. 78, “Cloning and sequence of cDNA coding for alpha1–antitrypsin”, pp. 6826–6830, 1981.*

Svendsen, I., et al., “Amino acid sequence of serine protease inhibitor Cl–1 from barley: Homology with barley inhibtor Ci–2, potato inhibitor I and leech eglin”, Chemical Abstracts, vol. 97, No. 51668j, 1982.*

Leicht, M., et al., Nature, vol. 297, “Sequence homology and structural comparison between the chromosomal human alpha1–antitrypsin and chicken ovalbumin genes”, pp. 655–659, 1982.*

Valenzuela, P., et al., Nature, vol. 298, “Synthesis and assembly of hepatitis B virus surface antigen particles in yeast”, pp. 347–350, 1982.*

Kurjan, J., et al., Cell, vol. 30, “Structure of a yeast pheromone gene (MFalpha): A putative alpha–factor precursor contains four tandem copies of mature alpha–factor”, pp. 933–934, 1982.*

Swift, G. H., et al., Proceedings of the National Academy of Sciences, U.S.A., vol. 79, “Rat pancreatic kallikrein mRNA: Nucleotide sequence and amino acid sequence of the encoded preproenzyme”, pp. 7623–7627, 1982.*

Maniatis, T., et al., Molecular Cloning: A Laboratory Manual, Cold Spring Harbor Laboratory Press, Procedures for cDNA cloning (excerpt), p. 231, 1982.*

Maniatis, T., et al., Molecular Cloning: A Laboratory Manual, Cold Spring Harbor Laboratory Press, “Extraction, purification, and analysis of mRNA from eukaryotic cells (excerpt)”, pp. 190–193, 1982.*

Botstein, D., et al., in The Molecular Biology of the Yeast *Saccharomyces*, Strathern, J. N., et al., Eds., Cold Spring Harbor Laboratory, “Principles and practice of recombinant DNA research with yeast”, pp. 607–636, 1982.*

Helfman, D. M., et al., Proceedings of the National Academy of Sciences, U.S.A., vol. 80, “Identification of clones that encode chicken tropomyosin by direct immunological screening of a cDNA expression library”, pp. 31–35, 1983.*

Young, R.A., et al., Proceedings of the National Academy of Sciences, U.S.A., vol. 80, “Efficient isolation of genes by using antibody probes”, pp. 1194–1198, 1983.*

Amann, E., et al., Gene, vol. 25, “Vectors bearing a hybrid trp–lac promoter useful for regulated expression of cloned genes in *Escherichia coli*”, pp. 167–178, 1983.*

Ohlsson, M., et al., Hoppe–Zeyler’s Z. Physiol. Chem., vol. 364, “Quantification of granulocyte elastase inhibitors in human mixed saliva and in pure parotid secretion”, pp. 1323–1328, 1983.*

Rogers, J., et al., Biochemical and Biophysical Research Communications, vol. 116, “The isolation of a clone for human alpha1–antitrypsin and the detection of alpha1–antitrypsin in mRNA from liver and leukocytes”, pp. 375–382, 1983.*

Anderson, s., et al., Proceedings of the National Academy of Sciences, U.S.A.,vol. 80, “Isolation of a genomic clone for bovine pancreatic trypsin inhibitor by using a unique–sequence synthetic DNA probe”, pp. 6838–6842, 1983.*

Emr, S. D., et al., Proceedings of the National Academy of Sciences, U.S.A., vol. 80, “An MFalpha1–SUC2 (alpha–factor–invertase) gene fusion for study of protein localization and gene expression in yeast”, pp. 7080–7084, 1983.*

Creighton, T. E., Proteins: Structures and Molecular Principles, Freeman & Company (Publ.), New York, pp. 93–94, 1983.*

Broach, J. R., Methods in Enzymology, vol. 101, “Construction of high copy yeast vectors using 2–um circle sequences”, pp. 307–325, 1983.*

Travis, J., et al., Annual Reviews in Biochemistry, vol. 52, “Human plasma proteinase inhibitors”, pp. 655–709, 1983.*

Alberts, B., et al., Molecular Biology of the Cell, Garland Publishing , Inc., New York, “Recombinant DNA Technology”, pp. 185–196, 1983.*

Ohlsson, M., et al., Acta Otolaryngolica, vol. 98, “Localization of antileukoproteinase in the parotid and the submandibular salivary glands”, pp. 147–151, 1984.*

Seto, S., et al., “The effect of aprotinin (a serine protease inhibitor) on renal function and renin release”, Chemical Abstracts, vol. 100, No. 46033z, 1984.*

Leytus, S. P., et al., Proceedings of the National Academy of Sciences, U.S.A., vol. 81, “Characterization of a cDNA coding for factor X”, pp. 3699–3702, 1984.*

Julius, D., et al., Cell, vol. 37, “Isolation of the putative structural gene for the lysine–arginine–cleafing endopeptidase required for processing ofthe yeast prepro–alpha–factor”, pp. 1075–1089, 1984.*

Derynk, R., et al., Cell, vol. 38, “Human transforming growth factor–alpha: Precursor structure and expression in *E. coli*”, pp. 287–297, 1984.*

Brake, A. J., et al., Proceedings of the National Academy of Sciences, U.S.A., vol. 81, “alpha–factor–directed synthesis and secretion of mature foreign proteins in *Saccharomyces cerevisiae*”, pp. 4642–4646, 1984.*

Landau, N. R., et al., Proceedings of the National Academy of Sciences, U.S.A., vol. 81, “Cloning of terminal transferase cDNA by antibody screening”, pp. 5836–5840, 1984.*

Ghrayeb, J., et al., The EMBO Journal, vol. 3, “Secretion cloning vectors in *Escherichia coli*”, pp. 2437–2442, 1984.*

Smith, C. E., et al., Biochemical Journal, vol. 225, “Human bronchial leucocyte proteinase inhibitor”, pp. 463–472, 1985.*

Klasen, E. C., et al., Biochemical and Biophysical Research Communications, vol. 128, "The N–terminal sequence of antileukoproteinase isolated from bronchial secretion", pp. 285–289, 1985.*

Whitson, P. A., et al., Biochemistry, vol. 25, "Dissociation of the lactose repressor–operator DNA complex: Effects of size and sequence context of operator–containing DNA", pp. 3845–3852, 1986.*

Whitson, P.A., et al., Biochemistry, vol. 25, "Thermodynamic analysis of the lactose repressor–operator DNA interaction", pp. 3852–3858, 1986.*

Seemüller, U., et al., FEBS Letters, vol. 199, "The acidstable proteinase inhibitor of human mucous secretions (HUSI–I, antileukoproteinase)", pp. 43–48, 1986.*

Chang, C. N., et al., Molecular and Cellular Biology, vol. 6, "*Saccharomyces cerevisiae* secretes and correctly processes human interferon hybrid proteins containing yeast invertase signal peptides", pp. 1812–1819, 1986.*

Thompson, R.C., et al., Proceedings of the National Academy of Sciences, U.S.A., vol. 83, "Isolation, properties, and complete amino acid sequence of human secretory leukocyte protease inhibitor, a potent inhibitor of leukocyte elastase", pp. 6692–6669, 1986.*

Stetler, G., et al., Nucleic Acids Research, vol. 14, "Isolation of a human gene encoding a potent inhibitor of leukocyte proteases", pp. 7883–7896, 1986.*

Van Arsdell, S. W., et al., Molecular and Cellular Biology, vol. 7, "The yeast repeated element sigma contains a hormone–inducible promoter", pp. 749–759, 1987.*

Fritz, H., Biological Chemistry Hoppe–Seyler, vol. 369, "Human mucus proteinase inhibitor (human MPI)", pp. 79–82, 1988.*

Hirsch, M. S., M.D., The American Journal of Medicine, vol. 85 (suppl 2A), "Antiviral drug development for the treantment of human immunodeficiency virus infections", pp. 182–185, 1988.*

Stetler, G.L., et al., Bio/Technology, vol. 7, "Secretion of active, full– and half–length human secretory leukocyte protease inhibitor by *Saccharomyces cerevisiae*", pp. 55–60, 1989.*

Lucey, E. C., et al., Journal of Laboratory and Clinical Medicine, vol. 115, "Recombinant human secretory leukocyte–protease inhibitor: In vitro properties, and amelioration of human neutrophil elastase–induced emphysema . . . ", pp. 224–232, 1990.*

Kramps, J. A., et al., Biochimica et Biophysica Acta, vol. 1038, "Proteinase inhibitory activities of antileukoprotease are represented by its second COOH–terminal domain", pp. 178–185, 1990.*

Böhm, B., et al., Biochemical Journal, vol. 274, "Purification of a serine–proteinase inhibitor from human articular cartilage", pp. 269–273, 1991.*

Birrer, P., et al., Journal of Applied Physiology, vol. 73, "Intravenous recombinant secretory leukoprotease inhibitor augments antineutrophil elastase defense", pp. 317–323, 1992.*

Anon., The Economist of Jan. 8, 1994, "Aids drugs: Beyond access", p. 79, 1994.*

Ebina et al., Protease inhibitors prevent the development of human rotavirus–induced diarrhea in suckling mice, Microbiol. Immunol., vol. 35 (7), 583–588 (1991).

Korant et al., Interactions between a viral protease and cystatins, Biol. Chem. Hoppe–Seyler, vol. 369, Suppl,. pp. 281–286 (1988).

McNeely et al., Secretory leukocyte protease inhibitor: a human saliva protein exhibiting anti–human immunodeficiency virus 1 activity in vitro, Journal of Clinical Investigation, vol. 96, pp. 456–464 (1995).

Weber et al., Molecular modeling of the HIV–1 protease and its substrate binding site, Science, vol. 243, pp. 928–931 (1989).

Proposed List of Preliminary Motions, filed by Sonoran Desert Chemicals LLC in Interference No. 104,792, Oct. 1, 2002.

Ohlsson et al. (1986), "Structure, Genomic Organization, and Tissue Distribution of Human Secretory Leukocyte–Protease Inhibitor (SLPI): A Potent Inhibitor of Neutrophil Elastase," *Pulmonary Emphysema and Proteolysis*, Academic Press, Inc., pp. 307–324.

Darnell et al. (1986), "Molecular Cell Biology," *Scientific American Books, Inc.*, pp. 54–55 and 158–260.

Ohlsson et al., *Chemical Abstracts*, (1983), No. 99:173443.

Rice et al., "Regulation of Proteolysis at the Neutrophil–Substrate Interface by Secretory Leukoprotease Inhibitor," *Science*, 249:178–181 (1990).

Schiessler et al., *Neutral Proteases of Human Polymorphonuclear Leukocytes*, Urban & Schwarzenberg, Baltimore/Munich, pp. 195–207 (1978).

Schiessler et al., "The Acid–stable Proteinase Inhibitor (Antileukoprotease) of Human Cervical Mucus," The Uterine Cervix in Reproduction, *Georg Thieme Publishers Stuttgart*, pp. 84–89 (1977).

Eisenberg, S.P., et al., "Location of the Protease–inhibitory Region of Secretory Leukocyte Protease Inhibitor," *The Journal of Biological Chemistry*, 265:7976–7981 (1990).

Wengenmayer, "Synthesis of Peptide Hormones Using Recombinant DNA Techniques," *Angew. Chem. Int. Ed. Engl.*, 22:842–858 (1983).

* cited by examiner

INHIBITION OF RETROVIRUS INFECTION

This application is a continuation-in-part of U.S. patent application Ser. No. 07/943,369, filed Sep. 9, 1992, now abandoned. This application is also a continuation-in-part of U.S. patent application Ser. No. 08/209,040, filed Mar. 9, 1994, now abandoned. This application is also a continuation-in-part of Patent Cooperation Treaty Application No. PCT/US93/08486, which was filed Sep. 9, 1993, and which designated the United States (Publication No. WO 94/06454).

This invention relates to the field of the treatment of retroviral infections and, more particularly, to the treatment of human immunodeficiency virus (HIV) infection and associated disease, including acquired immune deficiency syndrome (AIDS).

BACKGROUND OF THE INVENTION

Retroviral agents have been implicated in a number of diseases, including cancer, autoimmune disease and AIDS. Human immunodeficiency virus (HIV) infection causes chronic progressive depletion of $CD4^+$ T lymphocytes ($CD4^+$cells) and infection of macrophages, resulting in acquired immune deficiency syndrome. Currently zidovudine (AZT), an analogue of thymidine, is the primary anti-viral drug used in the treatment of HIV infection, although two other agents with a similar mechanism of action, dideoxyinosine (ddI) and dideoxycytosine (ddC), are also used. Colley, T. P. et al., New Engl. J. Med. (1990) 322:1340–45; Fischl, M. A., et al., New Engl. J. Med. (1987) 317:185–91. These agents are effective in inhibiting viral replication, and can stabilize the $CD4^+$cell levels, but they are unable to eliminate one of the major viral reservoirs, HIV infected macrophages. Gartner, S., et al., Science (1986) 233:215–19. Severe toxicity, particularly involving HIV host bone marrow is also associated with higher doses of AZT treatment, and the beneficial effects of the drug in AIDS patients diminishes after prolonged therapy; HIV strains resistant to AZT also have been observed in treated patients. These findings have prompted the search for alternative drugs for the treatment of HIV infection, particularly agents with a different mechanism of action.

Human immunodeficiency virus type 1 (HIV-1), a retrovirus, is the etiologic cause of AIDS. The HIV-1 envelope glycoprotein, gp120, specifically binds to the CD4 receptor on T lymphocytes and on monocytes and macrophages. Although infection of T lymphocytes requires cellular proliferation and DNA synthesis, productive infection of monocytes can occur independently of cellular DNA synthesis (Weinberg, J. B., et al, (1991) J. Exp. Med. 174:1477–82). When HIV-1 infects activated $CD4^+$ lymphocytes, it is lethal, but infected monocytes are relatively resistant to destruction by the virus. Consequently, these cells, once infected with HIV-1, serve as long-lived reservoirs of the virus. Not only are these cells a source of replicating virus, but their virally-mediated dysfunction may contribute to increased susceptibility to opportunistic infections that are the hallmark of AIDS.

Because monocyte-macrophages serve as reservoirs for HIV-1, selective targeting of this population, in addition to T lymphocytes, warrants further consideration (Finberg, R. W., et al., Science 252:1703–05, 1991. Early reports from Fox's group (JADA 118:709–711, 1989) indicated that a component of human saliva blocks HIV replication. More recently, Hattori (FEBS Lett. 248:48–52, 1989) showed that an inhibitor of tryptase (a trypsin-like enzyme) can inhibit syncytia formation of T-cells induced by HIV.

In exploring various potential modulators of HIV-1 infection, we have recently identified an endogenous source of inhibitory activity which retards HIV-1 infection and/or replication.

The factor responsible for the antiviral activity is serine leukocyte protease inhibitor (SLPI). SLPI is a potent inhibitor of human leukocyte elastase, chymotrypsin, cathepsin G, and of human trypsin, and has been purified from parotid secretions (Thompson, R. C. and K. Ohlsson, (1986) Proc. Natl. Acad. Sci. USA, 83:6692–96; and U.S. Pat. No. 4,760,130, both of which are incorporated herein by reference). SLPI is now available through production by recombinant DNA techniques; U.S. patent application Ser. No. 07/712,354, filed Jun. 7, 1991, PCT application No. WO86/03519, filed. Dec. 4, 1985, and European patent application 85 905 953.7, filed Dec. 4, 1985, each of which are incorporated herein by reference).

The ability of SLPI and/or its derivatives and analogs to block HIV-1 infection and/or replication can provide the basis for therapeutic intervention in HIV-1 infection.

SUMMARY OF THE INVENTION

The present invention provides novel methods for preventing or treating retroviral infections of mammalian cells, particularly preventing infection of human cells with human immunodeficiency virus (HIV) and associated diseases, including acquired immune deficiency syndrome (AIDS).

Included within the scope of this invention are pharmaceutical compositions for treating retroviral infections, particularly HIV infections in a human, comprising serine leukocyte protease inhibitor (SLPI), or an analog or derivative thereof, and a pharmaceutically acceptable carrier.

The invention also includes a method for treating HIV infections in a human cell comprising administering thereto an effective amount of SLPI or an analog or derivative thereof.

DETAILED DESCRIPTION OF THE INVENTION

Figure 1:
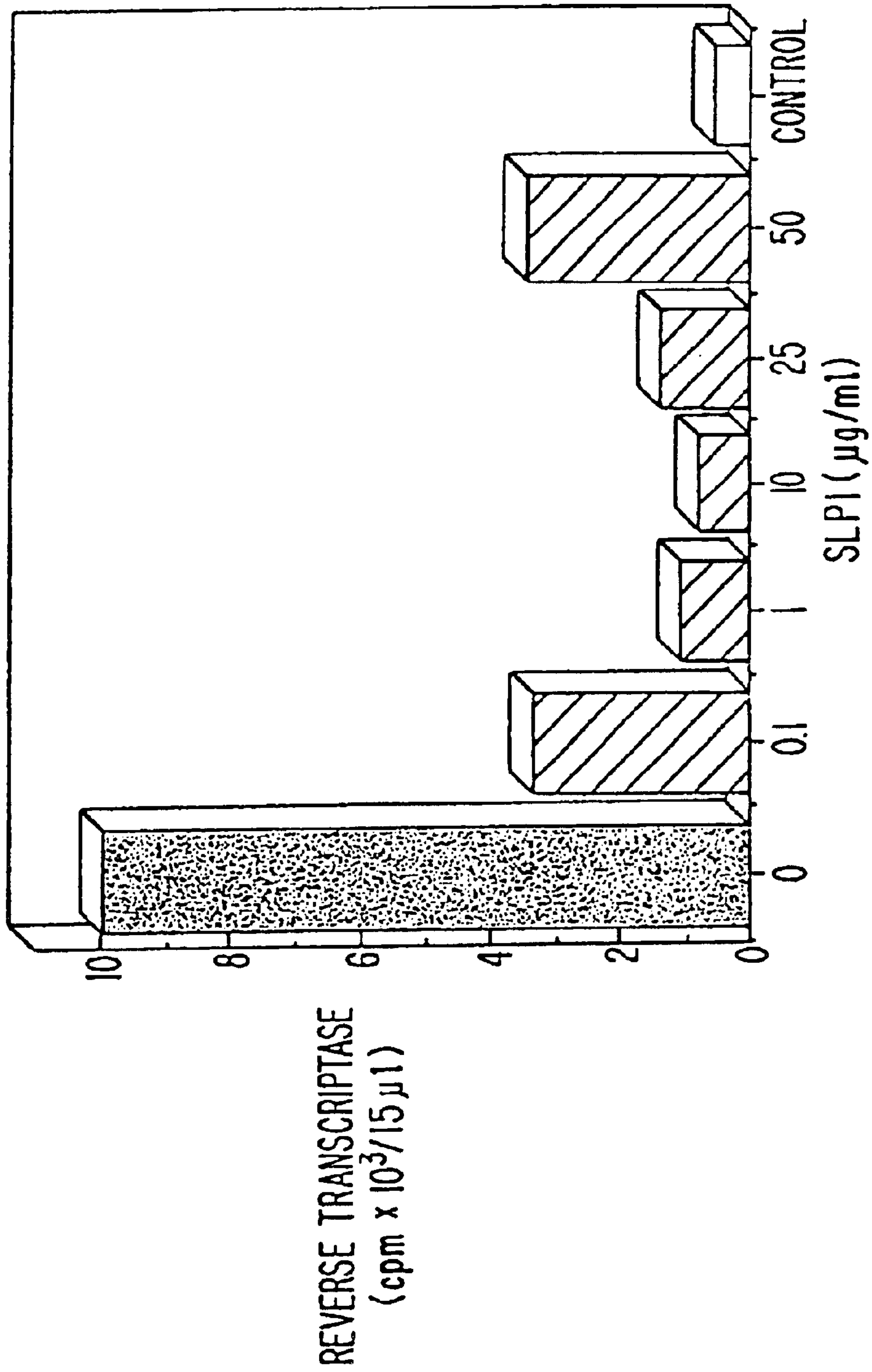
FIG. 1. SLPI blocks HIV replication in monocytes in a dose-dependent manner. Elutriated human monocytes were plated and exposed to HIV±SLPI for one hour at 37° C., washed, and incubated at 37° C., drawing off supernatants and adding fresh medium every four days. The $EC_{50}$ for this experiment was <0.1 μg/ml (8.5 nM) with complete inhibition at 10 μg/ml (850 nM).

The present invention provides methods for preventing retrovirus, particularly HIV infection of mammalian cells, particularly human cells, and associated diseases, including acquired immune deficiency syndrome (AIDS).

The term "pharmaceutically acceptable carrier" as used herein means a non-toxic, generally inert vehicle for the active ingredient, which does not adversely affect the ingredient or the patient to whom the formulation is administered.

The term "effective amount" as used herein means a pre-determined amount of SLPI, or an analog or derivative thereof, sufficient to be effective against HIV in vivo.

According to the present invention, retroviral infections are treated by administering anti-retroviral agents in doses sufficient to diminish the effects of such infection. Retroviral infections are implicated in a number of diseases, including but not limited to cancer, autoimmune disease, and acquired immune deficiency syndrome. Human immunodeficiency virus infection is of particular interest according to the present invention.

A variety of anti-retroviral agents are known in the art. Most of these inhibit the activity of retroviral reverse transcriptase and include zidovudine (AZT), an analogue of thymidine, dideoxyinosine (ddI), and dideoxycytosine (ddC). Zidovudine is the primary anti-viral drug used in the treatment of HIV infection. Anti-retroviral agents are generally efficacious in a dose ranging from about 50 mg/day to about 1000 mg/day, more particularly from about 100 mg/day to about 500 mg/day, and in the case of zidovudine, specifically about 300 mg/day to about 500 mg/day. These agents are generally administered in oral formulations.

The protease inhibitors used in this invention can be prepared by means well known to those skilled in the art (see, e.g., U.S. Pat. No. 4,760,130; European patent application 85 905 953.7, PCT application WO86/03519, and U.S. patent application Ser. No. 07/712,354, supra). The disclosed protease inhibitors include secretory protease inhibitors comprising the amino acid sequence of naturally-occurring secretory leukocyte protease inhibitor or a substitution analog comprising the amino acid sequence (SEQ ID NO:4):

R1-Gly-Lys-Ser-Phe-Lys-Ala-Gly-Val-Cys-Pro-Pro-Lys-Lys-Ser-Ala-Gln-Cys-Leu-R2-Tyr-Lys-Lys-Pro-Glu-Cys- Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-R8-R3-R9-Asn-Pro-Pro-Asn-Phe-Cys-Glu-R4-Asp-Gly-Gln-Cys-Lys-Arg-Asp-Leu-Lys-Cys-Cys-R5-Gly-R6-Cys-Gly-Lys-Ser-Cys-Val-Ser-Pro-Val-Lys-R7 wherein

R1 and R7 are the same or different and are selected from the group consisting of a substituted or unsubstituted amino acid residue or derivatives thereof; and R2, R3, R4, R5, R6, R8 and R9 are the same or different and are selected from the group consisting of methionine, valine, alanine, phenylalanine, tyrosine, tryptophan, lysine, glycine and arginine.

It is believed that minor alterations to the amino acid sequence at the C- and N-termini will not significantly alter the activity of the disclosed protease inhibitors. Specifically, substitution at the C- or N-terminus with a cyclized amino acid, for example, proline, is believed to result in a protease inhibitor having the desired serine protease inhibiting activity. Also, analogs of the disclosed protease inhibitors which have alterations at the C- or N-terminus, which alterations do not destroy the serine protease inhibitor properties of the analog, are included within the scope of the present invention.

The present invention relates to protease inhibitors which have been isolated in a purified form. Preferably, the serine protease inhibitors of the present invention are single-polypeptide-chain proteins which are substantially homologous to, and most preferably biologically equivalent to, the native serine protease inhibitor isolated from human parotid secretions. The native serine protease inhibitor is also referred to as the native parotid inhibitor. By "biologically equivalent" as used throughout the specification and claims, is meant that the compositions are capable of inhibiting the monocyte-derived or T-cell derived protease that is inhibited by SLPI, but not necessarily to the same degree. By "derivatives" as used throughout the ensuing specification and claims, is meant a degree of amino acid homology to the native parotid inhibitor, preferably in excess of 40%, most preferably in excess of 50%, with a particularly preferred group of proteins being in excess of 60% homologous with the native parotid inhibitor. The percentage homology, as above described, is calculated as the percentage of the components found in the smaller of the two sequences that may also be found in the larger of the two sequences, a component being understood as a sequence of four, contiguous amino acids.

One useful SLPI derivative is CLPI, a truncated SLPI molecule having only the last 60 amino acids of the native parotid inhibitor. These 60 amino acids are:

Leu Asp Pro Val Asp Thr Pro Asn Pro Thr Arg Arg Lys
Pro Gly Lys Cys Pro Val Thr Tyr Gly Gln Cys Leu Met
Leu Asn Pro Pro Asn Phe Cys Glu Met Asp Gly Gln Cys
Lys Arg Asp Leu Lys Cys Cys Met Gly Met Cys Gly Lys
Ser Cys Val Ser Pro Val Lys Ala. (SEQ. ID. NO.: 1)

The following nucleotide sequence has been used to encode the above 60 amino acid molecule:

CTG GAT CCT GTT GAC ACC CCA ACA CCA ACA AGG AGG AAG
CCT GGG AAG TGC CCA GTG ACT TAT GGC CAA TGT TTG ATG
CCT AAC CCC CCC AAT TTC TGT GAG ATG GAT GGC CAG TGC
AAG CGT GAC TTG AAG TGT TGC ATG GGC ATG TGT GGG AAA
TCC TGC GTT TCC CCT GTG AAA GCT. (SEQ. ID. NO.: 2)

CLPI has been constructed by deleting from the SLPI gene the signal sequence and the nucleotides corresponding to the first 47 amino acids of the mature SLPI protein as described in U.S. patent application Ser. No. 07/712,354. CLPI can also be made by the method of Example 8 described in both PCT application WO86/03519 and European patent application 85 905 953.7. Although Example 8 in these two applications recites a method of making SLPI, this method can also be used to make CLPI. CLPI can be used to generate antibodies useful in purifying SLPI. Antibodies can be produced, for example, by the methods discussed in E. Harlow & D. Lane, *Antibodies: A Laboratory Manual, pp.* 92–114 (Cold Springs Harbor Laboratory, 1988).

By "analogs" as used herein, is meant any compound, including, for example, small organic compounds, that are functionally biologically equivalent to SLPI in inhibiting HIV infection. Such derivatives and analogs can be isolated by means well known to those skilled in the art, including using monocyte cells or T cells to screen for compounds that prevent SLPI from binding thereto. Analogs may also include specific SLPI muteins that have at least equivalent, and in some cases, greater activity than the native protein. Particularly useful SLPI muteins include substitution of the following amino acids at the residue position enumerated: Gly 20, Gly 72, Val 72, and Phe 72.

CLPI muteins are also within the scope of the invention. CLPI muteins which correspond to the SLPI muteins Gly 72, Val 72, and Phe 72 are herein referred to as Gly 25, Val 25, and Phe 25. Some contemplated CLPI muteins have the following amino acid sequence:

| |
|---|
| Leu Asp Pro Val Asp Thr Pro Asn Pro Thr Arg Arg Lys<br>Pro Gly Lys Cys Pro Val Thr Tyr Gly Gln Cys $R_8$ $R_3$<br>$R_9$ Asn Pro Pro Asn Phe Cys Glu $R_4$ Asp Gly Gln Cys<br>Lys Arg Asp Leu Lys Cys Cys $R_5$ Gly $R_6$ Cys Gly Lys<br>Ser Cys Val Ser Pro Val Lys $R_7$ |

wherein R7 is alanine, and R3, R4, R5, R6, and R8 are the same or different amino acids and one or more of R3, R4, R5, R6, and R8 may be methionine, valine, alanine, phenylalanine, tyrosine, tryptophan, lysine, glycine, or arginine. (SEQ. ID. NO.: 3) Analogs also include, for example, PEGylated forms of SLPI or CLPI which may have improved therapeutic characteristics over the native SLPI protein. Muteins which may be suitable for PEGylation include those having a cysteine residue at positions 13, 23, 52, 58, 68, and/or 75 of SLPI and at the corresponding sites 5, 11, 21, and 28 in CLPI. Preparation of cysteine muteins for PEGylation is described in PCT application WO 92/16221, filed Mar. 13, 1992, which is specifically incorporated herein by reference. A useful step in mutein production can include a refolding step in which cysteine is added to the solution containing the protein. The cysteine can aid in refolding and can bond to the substituted free cysteine in the mutein. One may also isolate from monocytes or T cells the SLPI inhibitable protein (SIP) from human monocyte cells or human T cells using standard biochemical techniques well known to those skilled in the art and purify proteins having proteolytic activity which is inhibited by SLPI. After purifying the protein (and, if necessary, sequencing it, cloning its gene, and expressing it in host cells, i.e., recombinantly producing SIP), one can screen for inhibitors of SIP by means well known to those skilled in the art. Alternatively, one can determine its structure and design inhibitors therefrom, also by means well known to those skilled in the art.

When SLPI, or an analog or derivative thereof (collectively, the "compounds"), is used to combat HIV infections in a mammal, the compound can be administered orally, parenterally, or locally, in a vehicle comprising one or more pharmaceutically acceptable carriers, the proportion of which is determined by the solubility and chemical nature of the compound, chosen route of administration and standard biological practice.

Pharmaceutical compositions containing the compounds of the present invention can be prepared. These compounds can be in a pharmaceutically-acceptable carrier to form the pharmaceutical compositions of the present invention. The term "pharmaceutically acceptable carrier" as used herein means a non-toxic, generally inert vehicle for the active ingredient, which does not adversely affect the ingredient or the patient to whom the composition is administered. Suitable vehicles or carriers can be found in standard pharmaceutical texts, for example, in *Remington's Pharmaceutical Sciences,* 16th ed., Mack Publishing Co., Easton, Pa. (1980), incorporated herein by reference. Such carriers include, for example, aqueous solutions such as bicarbonate buffers, phosphate buffers, Ringer's solution and physiological saline. In addition, the carrier can contain other pharmaceutically-acceptable excipients for modifying or maintaining the pH, osmolarity, viscosity, clarity, color, sterility, stability, rate of dissolution, or odor of the formulation.

The pharmaceutical compositions can be prepared by methods known in the art, including, by way of an example, the simple mixing of reagents. Those skilled in the art will know that the choice of the pharmaceutical carrier and the appropriate preparation of the composition depend on the intended use and mode of administration.

In one embodiment, it is envisioned that the compound and pharmaceutically acceptable carrier constitute a physiologically-compatible, slow-release formulation. The primary solvent in such a carrier can be either aqueous or non-aqueous in nature. In addition, the carrier can contain other pharmacologically-acceptable excipients for modifying or maintaining the pH, osmolarity, viscosity, clarity, color, sterility, stability, rate of dissolution, or odor of the formulation. Similarly, the carrier can contain still other pharmacologically-acceptable excipients for modifying or maintaining the stability, rate of dissolution, release, or absorption of the compound. Such excipients are those substances usually and customarily employed to formulate dosages for oral, parenteral or local administration in either unit dose or multi-dose form.

Once the pharmaceutical composition has been formulated, it can be stored in sterile vials as a solution, suspension, gel, emulsion, solid, or dehydrated or lyophilized powder. Such formulations can be stored either in a ready to use form or requiring reconstitution immediately prior to administration.

The manner of administering the formulations containing the compounds for systemic delivery can be via subcutaneous, intramuscular, intravenous, oral, intranasal, or vaginal or rectal suppository. Administration of the formulations containing the compounds for local delivery includes via intraarticular, intratracheal, or instillation or inhalations to the respiratory tract. Local administration via vaginal or rectal suppository or topical application is also contemplated. In addition it may be desirable to administer the compounds to specified portions of the alimentary canal either by oral administration of the compounds in an appropriate formulation or device.

For oral administration, the compound can be formulated in unit dosage forms such as capsules or tablets each containing a predetermined amount of the active ingredient, ranging from about 10 to 1000 mg, more preferably 10–200 mg per day per patient, even more preferably 20–200 mg per day per patient, in a pharmaceutically acceptable carrier. The compound can be formulated with or without pharmaceutically-acceptable carriers customarily used in the compounding of solid dosage forms. Preferably, the capsule or tablet is designed so that the active portion of the formulation is released at that point in the gastro-intestinal tract when bioavailability is maximized and pre-systemic degradation is minimized. Additional excipients can be included to facilitate absorption of the compound. Diluents, flavorings, low melting point waxes, vegetable oils, lubricants, suspending agents, tablet disintegrating agents, and binders can also be employed.

For parenteral administration, the compound is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic. Subcutaneous injection is the preferred route of administration. Dosages are essentially the same as those set forth above for oral administration.

For local administration, the compound is preferably formulated to maximize the availability of the compound at the intended site of administration. Local administration of the compound at known or expected sites of entry or release of retrovirus into and from the body is particularly contemplated. For example, in consideration of the variety of mammalian sexual practices, topical administration of the compound to all orifices and interior or exterior genitalia is desirable. In addition, topical application to skin surfaces, and in particular to any skin interruptions such as cuts, abrasions, lesions, blisters and the like, is believed useful in preventing the exchange of retrovirus from one host to another.

In one particularly useful embodiment, gloves containing the compounds formulated for local administration are prepared for those who come into contact with hosts or bodily fluids. Preferred dosages for local administration include those for which a local compound concentration of 1–10 μg/ml is achieved.

In the case of systemic administration, the specific dose is typically calculated according to the approximate body weight of the patient. On the other hand, for local administration, the specific dose is typically not a function of the patient's body weight. Other factors in determining the appropriate dosage can include the disease or condition to be treated or prevented, route of administration and the age, sex and medical condition of the patient. Generally, treatment is initiated with small dosages substantially less than the optimum dose of the compound. Thereafter, the dosage is increased by small increments until the optimum effect under the circumstances is reached.

In general, the compound is most desirably administered at a concentration level that will generally afford antivirally effective results without causing any harmful or deleterious side effects. It is desirable to maintain a blood level of the compound at a level sufficient to inhibit retrovirus infection of the host cell. This can be estimated by assaying the amount of compound that is effective in preventing retroviral infection of host cells, e.g., HIV into monocytes, in vitro, and then, using standard pharmacokinetic techniques, determining the amount of compound required to keep plasma level at the same inhibitory level, or up to 10–100 times more. In certain embodiments, the dosage and administration is designed to create a preselected concentration range of the compound in the patient's blood stream. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. These dosages may be ascertained through use of the established assays for determining dosages utilized in conjunction with appropriate dose-response data.

Although the formulations disclosed hereinabove are effective and relatively safe medications for treating HIV infections, the possible concurrent administration of these formulations with antibacterial or other antiviral medications or agents to obtain beneficial results is not excluded. Such other antiviral medications or agents include soluble CD4, zidovudine, dideoxycytidine, phosphonoformate, ribavarin, antiviral interferons (e.g. alpha-interferon or interleukin-2) or aerosol pentamidine. Particularly useful antibacterial agents include those which target sexually-transmitted pathogens or the opportunistic pathogens often associated with retroviral infection.

It should be noted that the compound formulations described herein may be used for veterinary as well as human applications and that the term "patient" should not be construed in a limiting manner. In the case of veterinary applications, the dosage ranges should be the same as specified above.

It is also possible to utilize the nucleic acid sequences for SLPI themselves as therapeutic agents. For example, gene transfer methodologies can be employed to transfer a coding sequence for SLPI or an analog thereof to the patient where the gene can be replicated and expressed in vivo. Particularly useful gene therapy methods are discussed in the published international application WO 93/00051, which is specifically incorporated herein by reference.

Compositions containing the compounds useful for storing or treating instruments, devices, or the like which contact hosts or bodily fluids are also within the scope of the invention. Nonlimiting examples of such instruments, devices, or the like include needles, speculums, scalpels, surgical clips, or other articles which might penetrate a host or contact bodily fluids. Preferably, the compositions neither adversely affect the activity of the compounds contained therein nor adversely react with the articles to be treated or stored. Such compositions can be prepared by methods known in the art particularly in light of the information contained herein.

The invention also includes a method for inhibiting retrovirus infection by blocking the function of a host cell enzyme, which enzyme function is necessary for retrovirus infection of the cell. As stated above, SLPI is a potent inhibitor of elastase, trypsin, cathepsin G, and chymotrypsin.

The host cell enzyme can be an elastase-like enzyme. The term "elastase-like enzyme" as used herein means a protease which cleaves at the carboxy-terminal side of amino acids with small to medium sized hydrophobic side chains such as leucine, isoleucine, valine, and alanine.

The host cell enzyme can also be a chymotrypsin-like enzyme. As used herein, the term "chymotrypsin-like enzyme" means a protease which cleaves at the carboxy-terminal side of amino acids with medium to large hydrophobic side chains, including for example, phenylalanine, tyrosine, trytophan, leucine, and isoleucine.

A trypsin-like enzyme can also be a host cell enzyme. The term "trypsin-like" enzyme as used herein means a protease which cleaves at the carboxy-terminal side of basic amino acids including, for example, lysine and arginine.

In addition, cathepsin G can also be a host cell enzyme.

The invention is exemplified by the following illustrative examples:

EXAMPLE 1

Figure 2:
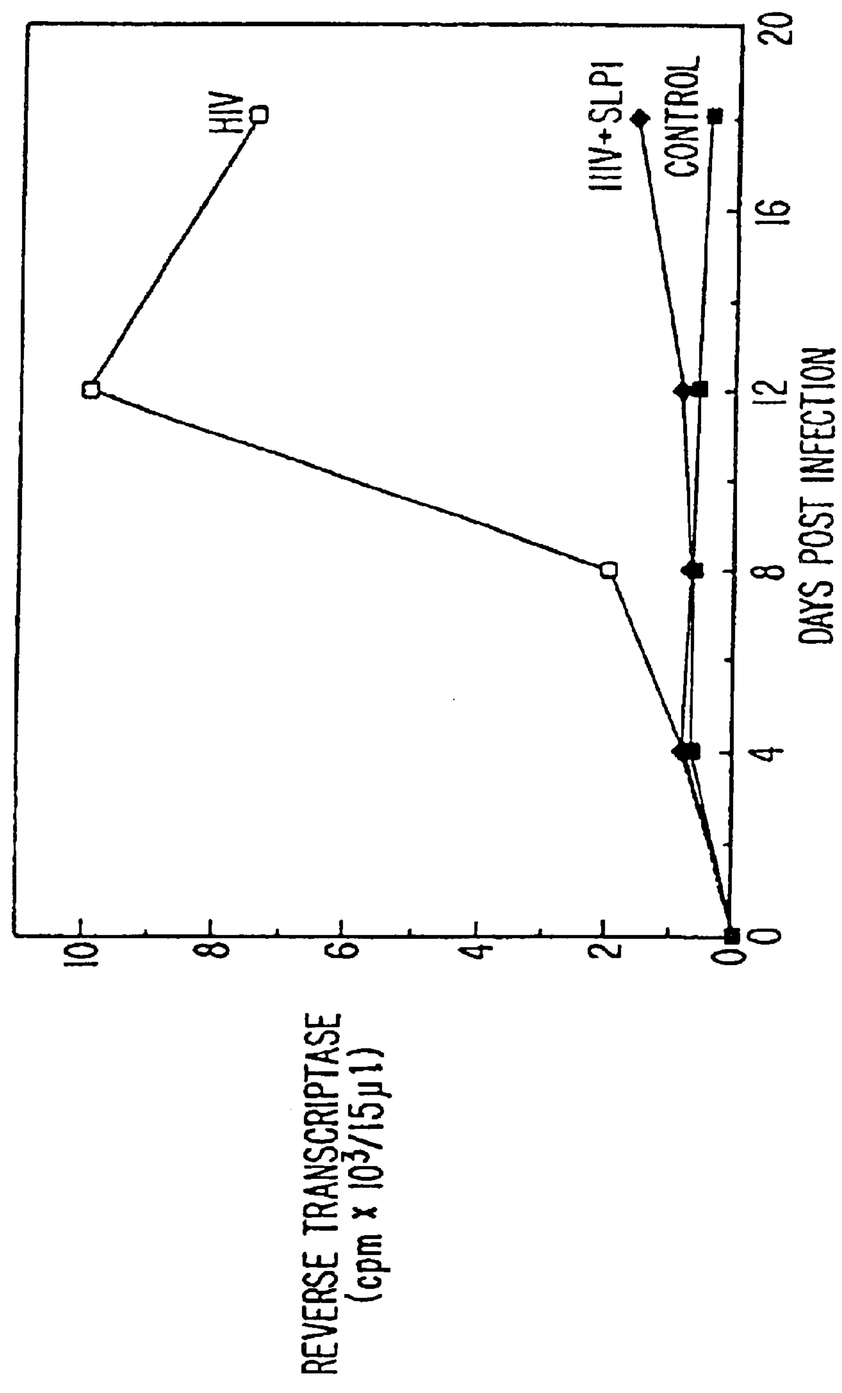
FIG. 2. The SLPI inhibitory effect is long-lasting. At the 18-day time point, HIV is still 90% inhibited.

Peripheral blood monocytes (PBM) were isolated from healthy donors by elutriation, plated in culture dishes, and incubated for several days. SLPI was mixed with HIV (Bal) and applied to PBM for one hour at 37° C. Cells were washed and incubated for additional time, with media changes and reverse transcriptase determinations on supernatants done every three days. We found that SLPI effectively blocks HIV replication at a concentration of 1 μg/ml (FIG. 1). At concentrations ≦20 μg/ml, SLPI inhibition is diminished. The inhibitory effect is long lasting, with significant inhibition seen out to 18 days (FIG. 2).

EXAMPLE 2

PBM were plated and incubated as in Example 1. SLPI was applied to cells for about one hour, cells were then washed, and treated with HIV. Medium was changed and assays done as in Example 1. We found that SLPI was more effective at blocking HIV when cells were pretreated with SLPI than when cells were treated with a mix of SLPI and HIV.

EXAMPLE 3

We have also demonstrated using essentially the same protocol as in Example 1, but substituting T-cells for monocytes, that SLPI is effective in inhibiting HIV replication in T-cells.

EXAMPLE 4

A human T-lymphocytic cell line (H-9) was maintained in suspension culture in RPMI 1640 with 10% fetal calf serum (FCS) and 200 micrograms per liter gentamicin. SLPI was added to the culture medium at a final concentration of 100 micrograms per milliliter. After 24 hours, cells were washed, inoculated for four hours with HIV strain IIIB, washed again, and resuspended at a density of 500,000 cells per milliliter. Media was supplemented and maintained with SLPI at a final concentration of 100 micrograms per milliliter immediately after resuspension (T=0) or 2 days after resuspension (T=2). Culture supernatant was collected and cultures were fed every 2 days. Supernatant collected 8 days after infection was assayed for reverse transcriptase activity by measuring uptake of tritiated thymidine onto a poly(rA)-oligo(dT) template.

As shown in Table 1, in SLPI pretreated cells, SLPI inhibited viral replication by approximately 62% and 54% when added immediately after infection and 2 days after infection, respectively.

TABLE 1

SLPI PRE-TREATED CELLS

| | Negative Control | Positive Control | T = 0 | T = 2 |
|---|---|---|---|---|
| RT Activity (mean cpm) | 955 | 86,205 | 32,594 | 39,554 |
| Standard Deviation | ± 330 | ± 9,676 | ± 7,220 | ± 8,737 |

EXAMPLE 5

The experiment was performed as described in Example 4 except that 1000-fold concentrated HIV strain IIIB was incubated with 100 micrograms per milliliter SLPI for 6 hours on ice prior to inoculation. This HIV/SLPI mixture was diluted 1000-fold prior to the four hour inoculation.

As shown in Table 2, using SLPI pre-treated virus and cells, SLPI inhibited viral replication by approximately 64% and 26% when added immediately after infection and 2 days after infection, respectively.

TABLE 2

SLPI PRE-TREATED VIRUS AND CELLS

| | Negative Control | Positive Control | T = 0 | T = 2 |
|---|---|---|---|---|
| RT Activity (mean cpm) | 2,889 | 59,004 | 20,676 | 43,432 |
| Standard Deviation | ± 565 | ± 10,988 | ± 4,111 | ± 14,982 |

EXAMPLE 6

The experiment was performed as in Example 5 except that cells were clean, i.e. not cultured with SLPI prior to inoculation. Using clean cells and SLPI pre-treated virus, SLPI inhibited viral replication by approximately 59% and 32% when added immediately after infection and 2 days after infection, respectively (Table 3).

TABLE 2

SLPI PRE-TREATED VIRUS

| | Negative Control | Positive Control | T = 0 | T = 2 |
|---|---|---|---|---|
| RT Activity (mean cpm) | 4,763 | 70,076 | 28,383 | 47,436 |
| Standard Deviation | ± 1,698 | ± 15,803 | ± 5,520 | ± 11,679 |

EXAMPLE 7

The experiment was performed as in Examples 4–6 except that neither cells nor virus were exposed to SLPI prior to inoculation. Using clean cells and clean virus, SLPI inhibited viral replication by approximately 50% and 42% when added immediately after infection and 2 days after infection, respectively (Table 4). Table 5 shows the reverse transcriptase activity which was present in culture supernatant assayed 4, 6, and 8 days after infection.

TABLE 4

CLEAN CELLS AND VIRUS

| | Negative Control | Positive Control | T = 0 | T = 2 |
|---|---|---|---|---|
| RT Activity (mean cpm) | 531 | 79,356 | 38,969 | 46,004 |
| Standard Deviation | ± 186 | ± 17,497 | ± 7,700 | +8,492 |

TABLE 5

CLEAN CELLS AND VIRUS

| | Negative Control | Positive Control | T = 0 | T = 2 |
|---|---|---|---|---|
| Day 4 (mean cpm) | 435 | 1,556 | 797 | 1,287 |
| Standard Deviation | ± 85 | ± 300 | ± 222 | ± 204 |
| Day 6 (mean cpm) | 952 | 72,085 | 15,846 | 41,240 |
| Standard Deviation | ± 715 | ± 12,219 | ± 5,644 | ± 14,542 |
| Day 8 (mean cpm) | 1,519 | 13,853 | 7,617 | 11,946 |
| Standard Deviation | ± 475 | ± 3,458 | ± 3,031 | ± 2,889 |

EXAMPLE 8

The effect of different SLPI muteins on viral replication was also investigated. Clean H-9 cells were incubated with clean virus for 4 hours as in Example 7. After washing, cells were resuspended at a density of 500,000 cells per milliliter in media containing 30 micrograms per milliliter SLPI or the SLPI muteins shown in Table 6. Culture supernatant was assayed for reverse transcriptase activity 8 days later (Table 6).

TABLE 6

| | Negative Control | Positive Control | Wild Type | Gly 20 | Gly 72 | Val 72 | Lys 72 | Phe 72 |
|---|---|---|---|---|---|---|---|---|
| RT Activity (mean cpm) | 4,815 | 55,126 | 39,323 | 39,387 | 40,549 | 36,077 | 52,239 | 8,384 |
| Standard Deviation | ±2,849 | ±6,637 | ±10,933 | ±11,143 | ±3,537 | ±7,859 | ±5,863 | ±1,924 |

EXAMPLE 9

The experiment was performed as in Example 8 except that after inoculation, cells were resuspended in media containing 100 micrograms per milliliter SLPI or the Phe 72 mutein. Culture supernatant was assayed for reverse transcriptase activity 2, 4, 6, 8, and 10 days post-infection (Table 7). Tables 6 and 7 show that the effect of the Phe-72 mutein was particularly pronounced.

TABLE 7

| | Negative | Positive | SLPI | PHE-72 |
|---|---|---|---|---|
| Day 2 (mean cpm) | | 1,386 | 995 | 897 |
| Standard Deviation | | ± 914 | ± 246 | ± 472 |
| Day 4 (mean cpm) | | 1,356 | 1,087 | 1,380 |
| Standard Deviation | | ± 370 | ± 414 | ± 442 |
| Day 6 (mean cpm) | 1,142 | 2,103 | 1,526 | 748 |
| Standard Deviation | ± 389 | ± 498 | ± 508 | ± 243 |
| Day 8 (mean cpm) | | 77,931 | 25,241 | 3,491 |
| Standard Deviation | | ± 9,779 | ± 8,399 | ± 1,086 |
| Day 10 (mean cpm) | | 21,431 | 12,499 | 2,239 |
| Standard Deviation | | ± 1,890 | ± 3,495 | ± 444 |

EXAMPLE 10

To determine the effect of SLPI alone, H-9 cell proliferation was evaluated by thymidine incorporation assays using 200,000 H-9 cells cultured with 100 micrograms per milliliter SLPI and without SLPI. Cultures were pulsed with media containing 2.5 microcuries of tritiated thymidine at day 0, 1, and 2; incorporated counts were measured on day 1, 2, and 3. As shown in Table 8, SLPI is not toxic to these cells.

TABLE 8

| | THYMIDINE UPTAKE (mean cpm) H-9 PROLIFERATION | | |
|---|---|---|---|
| | Day 1 | Day 2 | Day 3 |
| Control (− SLPI) | 20,860 | 67,401 | 53,326 |
| Standard Deviation | ± 581 | ± 2,529 | ± 3,783 |
| + SLPI 100 μg/ml | 20,437 | 61,892 | 54,592 |
| Standard Deviation | ± 1,503 | ± 216 | ± 2,781 |

EXAMPLE 11

We also investigated inhibition of viral production from chronically infected cells using the promonocytic cell line U1. Suspension cultures of U1 were maintained in RPMI with 10% FCS and 200 micrograms per liter gentamicin. Cells were harvested, washed, and suspended at a density of 2.5 million cells per milliliter. Suspended cells were cultured overnight in media containing 100 or 200 micrograms per milliliter SLPI or media alone. Virus was induced by addition of 13-phorbol-12-myristate acetate (PMA) to a final concentration of 1 micromolar. After 48 hours, cell culture supernatant was assayed for reverse transcriptase activity as in Examples 4–9. As shown in Table 9, SLPI significantly inhibited viral production from these chronically infected cells.

TABLE 9

| | − PMA − SLPI | − PMA + SLPI (200 μg/ml) | + PMA − SLPI | + PMA + SLPI (200 μg/ml) | + PMA + SLPI (100 μg/ml) |
|---|---|---|---|---|---|
| RT Activity (mean cpm) | 1,052 | 994 | 5,052 | 2,864 | 2,648 |
| Standard Deviation | ± 352 | ± 447 | ± 2,053 | ± 403 | ± 374 |

EXAMPLE 12

SLPI was shown to directly bind U937 cells, which are derived from a human monocyte cell line, and HuT78 cells, which are derived from a human T cell line. SLPI was radiolabelled with I-125, having a specific activity of 125 Curies per millimole, using the Bolton Hunter reagent. The labeled protein had normal anti-elastase and anti-trypsin activity. Activity against cathepsin G and chymotrypsin was not determined. Specific binding of radiolabelled SLPI ("*SLPI") was determined by mixing increasing concentrations of *SLPI with cells ($10^7$/ml), in the absence and presence of cold SLPI using the procedure set forth in Dripps et al., *J. Biol. Chem.*, Vol. 266, No. 16, pp. 10331–10336 (1991), specifically incorporated herein by reference. A Scatchard plot of the data, shown in Tables 10 and 11, gave an apparent $K_D$ of 2 nM for U937 cells and HuT78 cells. This shows that SLPI binds with high affinity to U937 cells and that the binding is physiologically relevant based on the concentration of SLPI in body fluids. Kramps, J. A. et al., *AM REV RESPIR DIS*, Vol. 129, pp. 959–963 (1984), specifically incorporated herein by reference.

TABLE 10

| HuT78 CELLS | | | | |
|---|---|---|---|---|
| pM *SLPI | specific cpm | bound pM | bound per free | sites bound per cell |
| 40 | 0 | not done | not done | not done |
| 80 | 30 | 0.75 | 0.0095 | 45 |
| 160 | 37 | 0.93 | 0.0058 | 56 |
| 320 | 101 | 2.53 | 0.0079 | 152 |
| 640 | 101 | 2.53 | 0.0039 | 152 |
| 1280 | 303 | 7.6 | 0.0059 | 458 |
| 2560 | 398 | 9.98 | 0.0039 | 501 |
| 5120 | 538 | 13.5 | 0.0026 | 813 |
| 10,240 | 1302 | 32.7 | 0.0032 | 1970 |
| 20,480 | 1210 | 30.3 | 0.0015 | 1825 |

TABLE 11

| U937 CELLS | | | | |
|---|---|---|---|---|
| pM *SLPI | specific cpm | bound *SLPI (pM) | bound per free | sites bound per cell |
| 40 | 380 | 9.5 | 0.311 | 572 |
| 80 | 543 | 13.6 | 0.205 | 819 |
| 160 | 1315 | 32.9 | 0.259 | 1,982 |
| 320 | 2621 | 65.7 | 0.258 | 3,957 |
| 640 | 4630 | 116.1 | 0.221 | 6,993 |
| 1280 | 8650 | 217 | 0.204 | 13,070 |
| 2560 | 13,500 | 339 | 0.153 | 20,418 |
| 5120 | 15,124 | 379 | 0.080 | 22,827 |
| 10,240 | 18,462 | 463 | 0.047 | 27,886 |
| 20,480 | 18,769 | 471 | 0.024 | 28,368 |

EXAMPLE 13

U937 cells were induced by 13-phorbol-12-myristate acetate ("PMA"). Hanson et al., *J. Biol. Chem.*, Vol. 265, pp. 1524–1530 (1990); and Welgus et al., *J. Clin. Invest.*, Vol. 77, pp. 1675–1681 (1986), specifically incorporated herein by reference, show that PMA induction of U937 cells reduces cathepsin G and elastase activity.

U937 cells at an initial concentration of 10,000 cells per ml were placed in two flasks. PMA was added to one flask at a final concentration of 25 ng per ml. After 48 hours, cells were harvested from both flasks. Using the method of Dripps et al., *J. Biol. Chem.*, Vol. 266, No. 16, pp. 10331–10336 (1991), and labelling with I-125, having a specific activity of 91.5 Curries per millimole, the number of SLPI binding sites was determined. A Scatchard plot of the data in Tables 12 and 13 shows the number of SLPI binding sites in the PMA induced cells was reduced by 70%. In this experiment, the $K_d$ in non-induced cells was 1.1 nM; The $K_d$ in PMA-induced cells was 1.0 nM. The reduction in the number of SLPI binding sites in the PMA-induced cells is consistent with SLPI binding to elastase and cathepsin G on the cell surface.

TABLE 12

| U937 CELLS-MINUS PMA | | | | |
|---|---|---|---|---|
| pM *SLPI | specific cpm | bound *SLPI (pM) | bound per free | sites bound per cell |
| 80 | 400 | 37 | 0.860 | 2,229 |
| 320 | 1,077 | 101 | 0.461 | 6,083 |
| 640 | 2,213 | 207 | 0.478 | 12,468 |
| 1280 | 4,234 | 396 | 0.448 | 23,851 |
| 2560 | 6,340 | 593 | 0.301 | 35,716 |
| 5120 | 7,989 | 748 | 0.171 | 45,052 |
| 10,240 | 9,022 | 844 | 0.090 | 50,834 |
| 20,480 | 9,783 | 915 | 0.047 | 55,110 |

TABLE 13

| U937 CELLS-PLUS PMA | | | | |
|---|---|---|---|---|
| pM *SLPI | specific cpm | bound (pM) | bound per free | sites bound per cell |
| 80 | 339 | 32 | 0.67 | 1,909 |
| 320 | 698 | 65 | 0.255 | 3,915 |

TABLE 13-continued

| U937 CELLS-PLUS PMA | | | | |
|---|---|---|---|---|
| pM *SLPI | specific cpm | bound (pM) | bound per free | sites bound per cell |
| 640 | 1,103 | 103 | 0.192 | 6,204 |
| 1,280 | 1,391 | 130 | 0.113 | 7,830 |
| 2,560 | 2,302 | 215 | 0.092 | 12,949 |
| 5,120 | 1,442 | 135 | 0.027 | 8,131 |
| 10,240 | 2,933 | 274 | 0.028 | 16,503 |
| 20,480 | 2,725 | 255 | 0.0126 | 15,358 |

EXAMPLE 14

The binding of SLPI to U937 and HuT78 cells was shown to be specific. *SLPI was competitively inhibited with cold SLPI to these intact cells using the procedure set forth in Dripps et al., *J. Biol. Chem.*, Vol. 266, No. 30, pp. 20311–20315 (1991), specifically incorporated by reference. The percentage of *SLPI that was bound at various nanomolar concentrations of cold SLPI is set forth in Table 14. Specific binding was not inhibited by other basic proteins or other protease inhibitors at the concentrations listed in Table 15.

TABLE 14

| COMPETITIVE INHIBITION OF *SLPI BINDING | | |
|---|---|---|
| SLPI (nM) | % *SLPI BOUND (U937) | % *SLPI BOUND (HuT78) |
| 0.00 | 94 | 100 |
| 0.024 | 100 | 88 |
| 0.078 | 101 | 90 |
| 0.25 | 92 | 69 |
| 0.80 | 77 | 62 |
| 2.6 | 55 | 56 |
| 8.2 | 24 | not done |
| 26 | 12 | 37 |
| 84 | 3.5 | 9.3 |
| 270 | 0.00 | 0.00 |
| 860 | 0.00 | 8.7 |
| 2750 | 0.50 | not done |

TABLE 15

| COMPETITION STUDY USING VARIOUS COMPOUNDS | | |
|---|---|---|
| COMPOUND | CONCENTRATION | COMMENTS |
| HPSTI | 2.7 μM | INHIBITS TRYPSIN |
| bFGF | 2.7 μM | STRONGLY BASIC PROTEIN |
| PMSF | 10 mM | INHIBITS TRYPSIN |
| BENZAMIDINE | 10 mM | INHIBITS TRYPSIN |
| APROTININ | 10 μM | INHIBITS TRYPSIN |
| LEUPEPTIN | 10 μM | INHIBITS TRYPSIN |
| ANTIPAIN | 10 μM | INHIBITS TRYPSIN |
| α-1-ANTITRYPSIN | 10 μM | INHIBITS TRYPSIN AND ELASTASE |
| PEPSTATIN A | 10 μM | INHIBITS PEPSIN |

EXAMPLE 15

SLPI muteins were also shown to competitively inhibit SLPI binding to U937 cells and HuT78 cells using the procedure set forth in Example 14. (Dripps et al., *J. Biol. Chem.*, Vol. 266, No. 30, pp. 20311–20315 (1991)). Table 16 shows the affinities, as expressed by dissociation constant, $K_d$, of SLPI and of various SLPI muteins for U937 and for HuT78 cells, as estimated by the Cheng-Prusoff relationship. The Cheng-Prusoff relationship is set forth in Dripps et al., *J. Biol. Chem.*, Vol. 266, No. 30, pp. 20311–20315 (1991). Tables 17 and 18 show the percentage of radiolabelled SLPI bound at various concentrations of cold SLPI and of SLPI muteins to U937 and HuT78 cells, respectively.

TABLE 16

AFFINITIES OF SLPI AND SLPI MUTEINS FOR U937 AND HuT78 CELLS

| MUTEIN | SLPI | GLY 72 | GLY 20 | LYS 72 | PHE 72 | VAL 72 |
|---|---|---|---|---|---|---|
| $K_d$ (nM) U937 | 2 | 400 | 3.5 | 2.5 | 2 | 30 |
| $K_d$ (nM) HuT78 | 2 | 200 | 13 | 200 | 3 | 9 |

TABLE 17

COMPETITION STUDY USING SLPI MUTEINS. % *SLPI BOUND TO U937 CELLS AT VARIOUS CONCENTRATIONS OF (COMPETITORS)

| nM COMPETITOR | % *SLPI BOUND (SLPI) | % *SLPI BOUND (GLY72) | % *SLPI BOUND (GLY20) | % *SLPI BOUND (LYS72) | % *SLPI BOUND (PHE72) | % *SLPI BOUND (VAL72) |
|---|---|---|---|---|---|---|
| 0 | 109 | 131 | 130 | 117 | 94 | 95 |
| 0.024 | 111 | 116 | 110 | 116 | not done | not done |
| 0.078 | 111 | 118 | 117 | 113 | not done | not done |
| 0.25 | 106 | 120 | 110 | 103 | not done | not done |
| 0.80 | 78 | 116 | 91 | 86 | 77 | 90 |
| 2.6 | 46 | 115 | not done | 71 | 51 | 80 |
| 8.2 | 22 | 117 | 49 | 39 | 22 | 78 |
| 26 | 11 | 112 | 28 | 21 | not done | not done |
| 84 | 7 | 101 | 11 | 10 | 4 | 48 |
| 270 | 5 | 75 | 6 | 6 | not done | not done |
| 860 | 4 | 53 | 5 | 5 | not done | not done |
| 2750 | 4 | 28 | 5 | 4 | 5 | 8 |

TABLE 18

COMPETITION STUDY USING SLPI MUTEINS. % *SLPI BOUND TO HuT78 CELLS AT VARIOUS CONCENTRATIONS OF (COMPETITORS)

| nM COMPETITOR | % *SLPI BOUND (SLPI) | % *SLPI BOUND (LYS72) | % *SLPI BOUND (GLY72) | % *SLPI BOUND (GLY20) | % *SLPI BOUND (PHE72) | % *SLPI BOUND (VAL72) |
|---|---|---|---|---|---|---|
| 0 | 100 | 100 | 100 | 100 | 100 | 100 |
| 0.80 | 79 | 105 | 108 | 109 | 69 | 93 |
| 2.6 | 76 | 118 | 105 | 91 | 90 | 96 |
| 8.2 | 57 | 116 | 85 | 103 | 57 | 81 |
| 84 | 27 | 86 | 110 | 50 | 36 | 43 |
| 2750 | 0 | 34 | 28 | 7 | 1 | 14 |

EXAMPLE 16

SLPI and SLPI muteins were shown were shown to bind plasma membranes derived from U937 cells. Membranes were prepared as follows. Cells treated with a 10 mM NaCl solution were disrupted in a cell homogenizer. The plasma membrane fraction was enriched using a 41% sucrose step gradient. The membrane band was isolated and washed three times in phosphate buffered saline. Competitive binding, using the competitors set forth in Tables 19 and 20, to these membranes was performed as in Example 14 except that specific complexes were captured using the filtering procedure of Slack, J. et al., *Biotechniques*, Vol. 7, pp. 1132–1138 (1989), specifically incorporated herein by reference.

The affinities ($K_d$), as estimated by the Cheng-Prusoff relationship, for SLPI, SLPI muteins, gp120, alpha-1 protease inhibitor ("α-1-PI"), and aprotinin are shown in Table 19. The percentage of radiolabelled SLPI that was bound at various concentrations of cold SLPI or SLPI muteins is shown in Table 20. These results show that gp120 can compete with SLPI binding to its target. α-1-PI and aprotinin can also compete but at reduced affinities. Since gp120 can be a substrate for the host cell enzyme, the ability of gp120 to compete can be hampered by its being cleaved.

TABLE 19

AFFINITIES OF SLPI AND SLPI MUTEINS FOR U937 MEMBRANES

| COMPOUND | $K_d$ (nM) |
|---|---|
| SLPI | 2 |
| PHE 72 | 1 |
| GLY 72 | 5 |
| GLY 20 | 5 |

TABLE 19-continued

| AFFINITIES OF SLPI AND SLPI MUTEINS FOR U937 MEMBRANES | |
|---|---|
| COMPOUND | $K_d$ (nM) |
| LYS 72 | 5 |
| VAL 72 | 19 |
| gp120 | 400 |
| α-1-PI | 1,000 |
| APROTININ | 10,000 |

TABLE 20

CPM *SLPI BOUND AT VARIOUS CONCENTRATIONS OF COMPETITOR

| COMPETITOR (nM) | 0 | 0.800 | 2.56 | 8.20 | 83.9 | 268 | 2750 |
|---|---|---|---|---|---|---|---|
| SLPI | 18700 | 14753 | 10969 | 5709 | 2068 | not done | 1682 |
| LYS72 | 18700 | 14194 | 12213 | 7615 | 3497 | 3235 | 5008 |
| GLY72 | 18700 | 14716 | 11994 | 7206 | 3711 | 2840 | 1785 |
| PHE72 | 18700 | 12419 | 8919 | 4257 | 1662 | 2585 | 1537 |
| VAL72 | 18700 | 14023 | 11616 | 9238 | 3381 | 1737 | 923 |
| GLY72 | 18700 | 14036 | 11337 | 7298 | 3944 | 2531 | 1433 |
| GLY20 | 18700 | 14915 | 11390 | 7395 | 2486 | 1620 | 1501 |
| bFGF | 18700 | 14010 | 13480 | 14464 | 14967 | 14354 | 14710 |
| LYSOZYME | 18700 | 15190 | 14659 | 15012 | 15477 | 14884 | 15948 |

EXAMPLE 17

The binding sites on U937 and HuT78 cells for the Phe72 mutein were characterized. Membranes from U937 and Hut78 cells, prepared as described in Example 16, were treated with 0.25% CHAPS detergent and centrifuged, dialyzed in 20 mM potassium phosphate, pH5.5, 0.25% CHAPS, and chromatographed on monoS column, and eluted with a linear salt gradient. Fractions were analyzed by their ability to bind to immobilized the Phe72 mutein on a BIAcore instrument. The BIAcore analytical system is available from Pharmacia Biosensor AB, Uppsala, Sweden. See, *Nature*, Vol. 361, pp. 186–187 (1993), specifically incorporated herein by reference.

From solubilized U937 membrane monoS fractions, 4 peaks of binding activity to the Phe72 mutein were seen; peak 1 was from the monoS column flowthrough, peak 2 and 3 comigrated on monoS with purified human neutrophil elastase ("HNE") obtained from Calbiochem, San Diego, Calif. Peak 4 appears to be cathepsin G based on comparison with the monoS profile of cathepsin G appearing in Maison, C. M. et al., *Journal of Immunology*, Vol. 147, pp. 921–926 (1991), specifically incorporated herein by reference.

From HuT78 membranes, 1 peak of binding activity to the Phe72 mutein was seen. This peak coeluted on monoS with the second peak of activity from U937 membranes.

Using reducing SDS-PAGE, Western blot analysis of these active peaks showed that peaks 2 and 3 from U937 and the single peak from Hut78 contain a 30 kDa protein that reacts with an anti-elastase polyclonal antibody obtained from Calbiochem.

Affinity chromatography of CHAPS solubilized U937 membranes on a Phe72 SLPI mutein affinity column, prepared using NHS-activated Superose, PC 3.2/2 obtained from Pharmacia Biotech Inc., Piscataway, N.J., resulted in isolation of a doublet of proteins with the same mobility on reducing SDS-PAGE as active peaks 2 and 3. NHS-activated Superose, PC 3.2/2 is described at page 8 in the Pharmacia Biotech Inc. *Biotechnology Products Catalog* 1994.

EXAMPLE 18

SLPI and SLPI muteins were shown to inhibit proteolysis of the HIV-1 envelope protein, gp120, by human neutrophil elastase ("HNE"). As stated above, gp120 specifically binds to the CD4 receptor on T lymphocytes and on monocytes and macrophages.

Inhibition of HNE proteolytic cleavage of gp120 was shown as follows. The gp120 (400 nM), obtained from American Bio-Technologies, Cambridge, Mass., was incubated with increasing HNE (0.1 to 100 nM) concentrations. Incubation at 37° for 30 min, with 10 nM HNE yielded primarily 2 bands on Western blot, using reducing SDS-PAGE and probing with an anti-gp120 polyclonal antibody from American Bio-Technologies. The bands had an approximate molecular weight of 50 kDa and 70 kDa. This limited HNE proteolysis was inhibited by an anti-V3 loop monoclonal antibody (0.2 to 4 μM), also obtained from American Bio-Technologies, and by SLPI and SLPI muteins Phe72, Gly72, and Lys72 (0.1 to 100 nM). The IC50 of Lys72 appeared to be higher than that of SLPI or the other SLPI muteins. This is consistent with the observation that the Lys72 mutein is less effective in inhibiting HIV replication than wild type SLPI, the Phe72, and Gly72 muteins. (See Table 6, Example 8, above).

Purified soluble CD4 (400 nM), obtained from American Bio-Technologies, did not inhibit this cleavage.

gp120 (400 nM) was also incubated at 37° for 30 min, with 10 nM cathepsin G and yielded different bands. This suggests that cathepsin G does not cleave gp120 in the V3 loop.

EXAMPLE 19

Radiolabelled SLPI ("*SLPI") was shown to bind to elutriated human peripheral blood monocytes ("PBM"). SLPI was radiolabelled using $Na^{125}I$, obtained from ICN, 2727 Campus Dr., Irving, Calif. 92715, and Iodogen, obtained from Pierce, Rockford, Ill., according to the manufacturers' directions. Radiolabelling yielded 1.3 microcuries per microgram of SLPI. PBM ($20\times10^6$) in 1 ml Dulbecco's-modified Eagle's medium ("DMEM") were incubated with 0.6 nM to 13.2 nM *SLPI for 1 hour at 37° C. Cells were then pelleted and washed 3 times with phosphate buffered saline ("PBS"). Cell pellets were resuspended in Laemmli sample buffer and the samples applied to a 14% polyacrylamide gels under reducing conditions. Gels were analyzed using a phosphor imager to detect $^{125}I$ emission.

Alternatively, PBM ($12\times10^6$) in 1 ml DMEM were incubated for 30 minutes at 4° C. with increasing amounts of *SLPI. Cells were layered onto a 20% sucrose cushion and centrifuged 4 times in an Eppendorf microfuge. Cell pellets were removed and analyzed for gamma emission. Nonspecific binding, determined by including a 1000-fold excess of unlabelled SLPI was subtracted from total binding to give specific binding.

*SLPI binding was dose dependent and saturable at approximately 0.5 micrograms/ml *SLPI. The *SLPI concentration required for half-maximal binding to PBM was determined to be approximately 10 nM. This value (10 nM) is similar to the $K_d$ of *SLPI for U937 cells (see Examples 12 and 13).

In addition, *SLPI was crosslinked to PBM. PBM ($4\times10^6$) in 200 $\mu$l DMEM were incubated at 37° C. for 1 hour with 1.5 $\mu$M *SLPI. Cells were spun down and washed 3 times at room temperature with PBS and resuspended in 100 $\mu$l PBS. Either 0.5 mM DSS or 0.5 mM $BS^3$, were added for 30 minutes at room temperature. DSS is an organic crosslinking agent; $BS^3$ is a water soluble crosslinking agent. Both cross-linking agents were obtained from Pierce, Rockford, Ill., After incubation with the crosslinking agent, the cells were spun down and resuspended in Laemmli sample buffer and analyzed on a 4–15% gradient polyacrylamide gel under reducing conditions. Gels were dried and emission analyzed using a phosphor imager. Control samples for cross-linking consisted of *SLPI and cross-linking agent without monocytes.

In gels of crosslinked monocytes, using either cross-linking agent, one major crosslinked band appeared. This band was not seen in the control samples. Under reducing and nonreducing conditions, the molecular weight of the band was approximately 30 kDa. This molecular weight is consistent with the binding of SLPI (12 kDa) to elastase (25 kDa).

EXAMPLE 20

Using antibody staining, elastase was shown to be present on the surface of human monocytes. Purified rabbit polyclonal antibody to human neutrophil elastase ("Anti-HNE") was obtained from Calbiochem, LaJolla, Calif. Anti-HNE was conjugated to fluorescein isothiocyanate ("FITC") using the procedure set forth in *Current Protocols in Immunology,* 5.3.2–5.3.3, Coligan et al. eds. (1993), specifically incorporated herein by reference. Elutriated human monocytes were stained with either FITC-conjugated IgG (control antibody), FITC-conjugated anti-HNE ("FITC-anti-HNE"), or FITC-conjugated antibody against the monocyte marker, CD14. Control IgG antibody and FITC-conjugated anti-CD14 antibody were obtained from Becton Dickinson, San Jose, Calif.

The cells ($0.5\times10^6$ in 50 $\mu$l buffer) stained positive in a dose-related manner using 1 $\mu$g/ml–50 $\mu$g/ml anti-HNE. Staining by the anti-CD14 antibody confirmed that the cells were monocytes. No staining was seen with the control IgG.

EXAMPLE 21

In cross-linking experiments, SLPI did not directly interact with HIV-1. In separate experiments, approximately equal amounts of HIV-1 strains IIIB or BAL were incubated with 1 $\mu$M radiolabelled SLPI (*SLPI) in 200 $\mu$l DMEM for 1 hour at 37° C. After 1 hour, crosslinking reagent DSS (see Example 19) was added and incubation continued for 30 minutes at room temperature. Incubation was stopped by addition of Laemmli sample buffer. No attempt was made to remove free *SLPI from virus. Samples were applied to a 12% polyacrylamide gel run under reducing conditions. In a parallel sample, 2 $\mu$M *SLPI was crosslinked in the absence of virus. The volume of the parallel sample that was loaded on the gel was 5 times larger than the volume of the virus-containing samples. Gels were dried and analyzed using a phosphor imager to detect $^{125}I$ emission. No crosslinked products were detected in the viral samples. Only free *SLPI was observed. In the parallel sample, multiple crosslinked bands (SLPI crosslinked to itself) were seen.

EXAMPLE 22

SLPI was shown to neither activate nor inhibit monocyte activation by lipopolysaccharide ("LPS"). Elutriated human monocytes ($5\times10^6$/ml in DMEM with 10% human serum) were incubated overnight at 37° C., in the presence of 5% $CO_2$ with:

(1) medium alone (control);

(2) 1 $\mu$g/ml LPS;

(3) SLPI at 1 $\mu$g/ml, 10 $\mu$g/ml, or 100 $\mu$g/ml; or (4) 1 $\mu$g/ml LPS plus SLPI at 10 $\mu$g/ml or 100 $\mu$g/ml.

After overnight incubation, the cells from each of the seven groups were divided into 4 aliquots and stained using FITC-conjugated antibodies against three cell surface antigens and an FITC-conjugated IgG as a control. The three surface antigens probed were (1) interleukin 2 receptor. (IL-2R), (2) CD4; and 3) CD14.

The stained cells were analyzed by fluorescence-activated cell sorting ("FACS") and the results are shown in Table 21. The percent of cells labelled was calculated by percent labelled with specific antibody minus percent labelled with non-specific control antibody.

Control cells stained negative for IL-2R, which is a marker for cell activation. Control cells stained slightly positive for CD4 and positive for CD14, a monocyte marker.

Cells incubated overnight with LPS were activated, as demonstrated by positive IL-2R staining. In the LPS-activated cells, the CD4 staining disappeared and CD14 remained positive.

Cells incubated with SLPI in the absence of LPS stained negative for IL-2R. Thus, SLPI did not activate the monocytes. Cells incubated with SLPI and LPS, however, stained positive for IL-2R. Thus, SLPI did not interfere with LPS activation of monocytes.

TABLE 21

FACS ANALYSIS OF SLPI EFFECT ON MONOCYTE CELL SURFACE ANTIGENS

| CELL TREATMENT | IL-2R | CD4 | CD14 |
|---|---|---|---|
| CONTROL | neg. | 28.3% | 93% |
| LPS (1 $\mu$g) | 124% | neg. | 131% |
| SLPI (1 $\mu$g) | neg. | 30.5% | 87.9% |
| SLPI (10 $\mu$g) | neg. | 27.4% | 115% |
| SLPI (100 $\mu$g) | neg. | 32.2% | 104% |
| LPS (1 $\mu$g) + SLPI (10 $\mu$g) | 132.2% | neg. | 104.5% |
| LPS (1 $\mu$g) + SLPI (100 $\mu$g) | 131.2% | neg. | 137% |

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method for the inhibition of viral proliferation which comprises treating a patient with a composition containing an antiviral effective amount of a serine protease inhibitor comprising the amino acid sequence set forth in SEQ ID NO:4:

R1-Gly-Lys-Ser-Phe-Lys-Ala-Gly-Val-Cys-Pro-Pro- Lys-Lys-Ser-Ala-Gln-Cys-Leu-R2-Tyr-Lys-Lys-Pro- Glu-Cys-Gln-Ser-Asp-Trp-Gln-Cys-Pro-Gly-Lys-Lys- Arg-Cys-Cys-Pro-Asp-Thr-Cys-Gly-Ile-Lys-Cys-Leu- Asp-Pro-Val-Asp-Thr-Pro-Asn-Pro-Thr-Arg-Arg-Lys- Pro-Gly-Lys-Cys-Pro-Val-Thr-Tyr-Gly-Gln-Cys-R8-R3-R9-Asn-Pro-Pro-Asn-Phe-Cys-Glu-R4-Asp-Gly-Gln-Cys-Lys-Arg-Asp-Leu-Lys-Cys-Cys-R5-Gly-R6 Cys-Gly-Lys-Ser-Cys-Val-Ser-Pro-Val-Lys-R7 wherein

R1 and R7 are the same or different and are an amino acid residue;

R2, R3, R4, R5 and R6 are the same or different and are selected from the group consisting of methionine, valine, alanine, phenylalanine, tyrosine, tryptophan, lysine, glycine and arginine; and R8 and R9 are the same or different and are selected from the group consisting of methionine, valine, alanine, phenylalanine, tyrosine, tryptophan, lysine, glycine, leucine and arginine.

2. The method of claim 1, wherein said serine protease inhibitor is administered intravenously.

3. The method of claim 1, wherein said serine protease inhibitor is administered subcutaneously.

4. The method according to claim 1, wherein said serine protease inhibitor has phenylalanine at position R8.

5. The method according to claim 1, wherein said serine protease inhibitor has glycine at position R2.

6. The method according to claim 1, wherein said serine protease inhibitor has glycine at position R8.

7. The method according to claim 1, wherein said serine protease inhibitor has valine at position R8.

8. The method according to claim 1, further comprising administering at least one additional antiviral or antibacterial agent.

9. The method according to claim 1, wherein said serine protease inhibitor is covalently linked to polyethylene glycol.

10. The method according to claim 1, wherein said serine protease inhibitor has serine at position R1, arginine at position R2, methionine at position R3, methionine at position R4, methionine at position R5, methionine at position R6, alanine at position R7, leucine at position R8, and leucine at position R9.

11. A method for the inhibition of retroviral proliferation which comprises treating a patient with a composition containing an antiretroviral effective amount of a serine protease inhibitor comprising the amino acid sequence set forth in SEQ ID NO:4:

R1-Gly-Lys-Ser-Phe-Lys-Ala-Gly-Val-Cys-Pro-Pro-Lys-Lys-Ser-Ala-Gln-Cys-Leu-R2-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp-Pro-Val-Asp-Thr-Pro-Asn-Pro-Thr-Arg-Arg-Lys-Pro-Gly-Lys-Cys-Pro-Val-Thr-Tyr-Gly-Gln-Cys-R8-R3-R9-Asn-Pro-Pro-Asn-Phe-Cys-Glu-R4-Asp-Gly-Gln-Cys-Lys-Arg-Asp-Leu-Lys-Cys-Cys-R5-Gly-R6 Cys-Gly-Lys-Ser-Cys-Val-Ser-Pro-Val-Lys-R7 wherein

R1 and R7 are the same or different and are an amino acid residue;

R2, R3, R4, R5 and R6 are the same or different and are selected from the group consisting of methionine, valine, alanine, phenylalanine, tyrosine, tryptophan, lysine, glycine and arginine; and R8 and R9 are the same or different and are selected from the group consisting of methionine, valine, alanine, phenylalanine, tyrosine, tryptophan, lysine, glycine, leucine and arginine.

12. The method according to claim 11, wherein the retrovirus is a human immunodeficiency virus (HIV).

13. The method according to claim 12, wherein the HIV is HIV-1.

14. The method of claim 11, wherein said serine protease inhibitor is administered intravenously.

15. The method of claim 11, wherein said serine protease inhibitor is administered subcutaneously.

16. The method according to claim 11, wherein said serine protease inhibitor has phenylalanine at position R8.

17. The method according to claim 11, wherein said serine protease inhibitor has glycine at position R2.

18. The method according to claim 11, wherein said serine protease inhibitor has glycine at position R8.

19. The method according to claim 11 wherein said serine protease inhibitor has valine at position R8.

20. The method according to claim 11, further comprising administering at least one additional antiviral or antibacterial agent.

21. The method according to claim 11, wherein said serine protease inhibitor is covalently linked to polyethylene glycol.

22. The method according to claim 11, wherein said serine protease inhibitor has serine at position R1, arginine at position R2, methionine at position R3, methionine at position R4, methionine at position R5, methionine at position R6, alanine at position R7, leucine at position R8, and leucine at position R9.

* * * * *

SEQUENCE LISTING

<160> NUMBER OF SEQ ID NOS: 4

<210> SEQ ID NO 1
<211> LENGTH: 60
<212> TYPE: PRT
<213> ORGANISM: Artificial Sequence
<220> FEATURE:
<223> OTHER INFORMATION: Description of Artificial Sequence: Synthetic
CLPI amino acid sequence

<400> SEQUENCE: 1

```
Leu Asp Pro Val Asp Thr Pro Asn Pro Thr Arg Arg Lys Pro Gly Lys
  1               5                  10                  15

Cys Pro Val Thr Tyr Gly Gln Cys Leu Met Leu Asn Pro Pro Asn Phe
             20                  25                  30

Cys Glu Met Asp Gly Gln Cys Lys Arg Asp Leu Lys Cys Cys Met Gly
         35                  40                  45

Met Cys Gly Lys Ser Cys Val Ser Pro Val Lys Ala
     50                  55                  60
```

<210> SEQ ID NO 2
<211> LENGTH: 180
<212> TYPE: DNA
<213> ORGANISM: Artificial Sequence
<220> FEATURE:
<223> OTHER INFORMATION: Description of Artificial Sequence: Synthetic
nucleotide sequence encoding CLPI

<400> SEQUENCE: 2

```
ctggatcctg ttgacacccc aacaccaaca aggaggaagc ctgggaagtg cccagtgact     60

tatggccaat gtttgatgcc taacccccc aatttctgtg agatggatgg ccagtgcaag    120

cgtgacttga agtgttgcat gggcatgtgt gggaaatcct gcgtttcccc tgtgaaagct    180
```

<210> SEQ ID NO 3
<211> LENGTH: 60
<212> TYPE: PRT
<213> ORGANISM: Artificial Sequence
<220> FEATURE:
<221> NAME/KEY: MOD_RES
<222> LOCATION: (25)..(26)
<223> OTHER INFORMATION: Variable amino acid
<220> FEATURE:
<221> NAME/KEY: MOD_RES
<222> LOCATION: (27)
<223> OTHER INFORMATION: Variable amino acid
<220> FEATURE:
<221> NAME/KEY: MOD_RES
<222> LOCATION: (35)
<223> OTHER INFORMATION: Variable amino acid
<220> FEATURE:
<221> NAME/KEY: MOD_RES
<222> LOCATION: (47)
<223> OTHER INFORMATION: Variable amino acid
<220> FEATURE:
<221> NAME/KEY: MOD_RES
<222> LOCATION: (49)
<223> OTHER INFORMATION: Variable amino acid
<220> FEATURE:
<223> OTHER INFORMATION: Description of Artificial Sequence: Synthetic
CLPI mutein sequence

<400> SEQUENCE: 3

```
Leu Asp Pro Val Asp Thr Pro Asn Pro Thr Arg Arg Lys Pro Gly Lys
  1               5                  10                  15

Cys Pro Val Thr Tyr Gly Gln Cys Xaa Xaa Xaa Asn Pro Pro Asn Phe
```

-continued

```
            20                  25                  30

Cys Glu Xaa Asp Gly Gln Cys Lys Arg Asp Leu Lys Cys Cys Xaa Gly
        35                  40                  45

Xaa Cys Gly Lys Ser Cys Val Ser Pro Val Lys Ala
    50                  55                  60


<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (1)
<223> OTHER INFORMATION: A substituted or unsubstituted amino acid
      residue
<220> FEATURE:
<221> NAME/KEY: MOD_RES
<222> LOCATION: (20)
<223> OTHER INFORMATION: Met, Val, Ala, Phe, Tyr, Trp, Lys, Gly or Arg
<220> FEATURE:
<221> NAME/KEY: MOD_RES
<222> LOCATION: (72)
<223> OTHER INFORMATION: Met, Val, Ala, Phe, Tyr, Trp, Lys, Gly, or Arg
<220> FEATURE:
<221> NAME/KEY: MOD_RES
<222> LOCATION: (73)
<223> OTHER INFORMATION: Met, Val, Ala, Phe, Tyr, Trp, Lys, Gly or Arg
<220> FEATURE:
<221> NAME/KEY: MOD_RES
<222> LOCATION: (74)
<223> OTHER INFORMATION: Met, Val, Ala, Phe, Tyr, Trp, Lys, Gly, or Arg
<220> FEATURE:
<221> NAME/KEY: MOD_RES
<222> LOCATION: (82)
<223> OTHER INFORMATION: Met, Val, Ala, Phe, Tyr, Trp, Lys, Gly or Arg
<220> FEATURE:
<221> NAME/KEY: MOD_RES
<222> LOCATION: (94)
<223> OTHER INFORMATION: Met, Val, Ala, Phe, Tyr, Trp, Lys, Gly or Arg
<220> FEATURE:
<221> NAME/KEY: MOD_RES
<222> LOCATION: (96)
<223> OTHER INFORMATION: Met, Val, Ala, Phe, Tyr, Trp, Lys, Gly or Arg
<220> FEATURE:
<221> NAME/KEY: MOD_RES
<222> LOCATION: (107)
<223> OTHER INFORMATION: A substituted or unsubstituted amino acid
      residue

<400> SEQUENCE: 4

Xaa Gly Lys Ser Phe Lys Ala Gly Val Cys Pro Pro Lys Lys Ser Ala
  1               5                  10                  15

Gln Cys Leu Xaa Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Xaa Xaa Xaa Asn Pro Pro Asn Phe Cys
 65                  70                  75                  80

Glu Xaa Asp Gly Gln Cys Lys Arg Asp Leu Lys Cys Cys Xaa Gly Xaa
                 85                  90                  95

Cys Gly Lys Ser Cys Val Ser Pro Val Lys Xaa
            100                 105
```